(12) United States Patent
Ghazzawi

(10) Patent No.: US 10,780,318 B1
(45) Date of Patent: Sep. 22, 2020

(54) BREATHING DEVICE WITH EXHALE AND INHALE VALVE TO CREATE RESISTANCE

(71) Applicant: Firas Kasem Ghazzawi, Omaha, NE (US)

(72) Inventor: Firas Kasem Ghazzawi, Omaha, NE (US)

( * ) Notice: Subject to any disclaimer, the term of this patent is extended or adjusted under 35 U.S.C. 154(b) by 0 days.

(21) Appl. No.: 16/388,755

(22) Filed: Apr. 18, 2019

(51) Int. Cl.
*A63B 23/18* (2006.01)
*A61M 16/04* (2006.01)
*A61M 16/20* (2006.01)

(52) U.S. Cl.
CPC ......... *A63B 23/18* (2013.01); *A61M 16/0488* (2013.01); *A61M 16/208* (2013.01)

(58) Field of Classification Search
CPC ........ A63B 21/00058; A63B 21/00069; A63B 21/00076; A63B 21/008; A63B 21/0085; A63B 21/0088; A63B 21/4003; A63B 21/4027; A63B 21/4039; A63B 23/025; A63B 23/03; A63B 23/032; A63B 23/18; A63B 23/185; A63B 69/0057; A63B 69/0059; A63B 71/0054; A63B 71/08; A63B 71/085; A63B 2071/0072; A63B 2071/086; A63B 2225/09; A61M 16/0488; A61M 16/208
See application file for complete search history.

(56) References Cited

U.S. PATENT DOCUMENTS

| 3,695,608 | A | | 10/1972 | Hanson | |
|---|---|---|---|---|---|
| 4,739,987 | A | | 4/1988 | Nicholson | |
| 4,973,047 | A | * | 11/1990 | Norell | A63B 23/18 482/13 |
| 5,598,839 | A | * | 2/1997 | Niles | A61M 16/08 128/205.23 |
| 5,658,221 | A | * | 8/1997 | Hougen | A63B 23/18 482/13 |
| 5,899,832 | A | * | 5/1999 | Hougen | A63B 23/18 128/200.24 |
| 6,083,141 | A | * | 7/2000 | Hougen | A61M 16/0006 128/202.16 |
| D440,651 | S | * | 4/2001 | Foran | D24/110 |
| 6,500,095 | B1 | | 12/2002 | Hougen | |
| 6,581,598 | B1 | | 6/2003 | Foran et al. | |
| D594,969 | S | * | 6/2009 | Marquis | D24/110 |

(Continued)

FOREIGN PATENT DOCUMENTS

WO 9852651 A1 11/1998

OTHER PUBLICATIONS

"Smart Breathe device—yoga for modern people", http://smart-breathe.com/homepage/, 59 pages, accessed Sep. 11, 2019.

*Primary Examiner* — Gary D Urbiel Goldner
(74) *Attorney, Agent, or Firm* — McKee, Voorhees & Sease, PLC

(57) ABSTRACT

A breathing device meant to improve the respiratory system of a user includes a mouthpiece, a front piece, an inhale ring, a middle piece, an insert slider, and an exhale ring. The insert slider is slidable between an inhale position and an exhale position. Various grooves, bumps, slots, ribs mate with, engage, slide, and rotate with respect to one another to allow a user to adjust the amount of airflow through the breathing device. The breathing device disclosed herein is easy to assemble, to use, and to adjust to varying levels of resistance.

19 Claims, 11 Drawing Sheets

(56) References Cited

U.S. PATENT DOCUMENTS

| | | | |
|---|---|---|---|
| 8,074,642 B2 * | 12/2011 | Bruce | A61M 15/009 128/200.23 |
| 10,245,397 B2 | 4/2019 | Kashefi-Khorasani et al. | |
| 10,272,215 B2 | 4/2019 | Adams et al. | |
| 10,314,991 B2 | 6/2019 | Robitaille et al. | |
| 10,322,312 B1 | 6/2019 | Danford | |
| 10,328,293 B2 | 6/2019 | Dickstein et al. | |
| 10,413,698 B2 | 9/2019 | Meyer et al. | |
| 10,434,277 B2 * | 10/2019 | Warner | A61M 16/209 |
| 2002/0029779 A1 * | 3/2002 | Schmidt | A61M 15/0018 128/205.25 |
| 2007/0089740 A1 * | 4/2007 | Baumert | A61M 16/0488 128/203.12 |
| 2010/0206310 A1 * | 8/2010 | Matsubara | A61M 16/0833 128/205.24 |
| 2012/0186585 A1 * | 7/2012 | Richards | A61M 16/209 128/203.12 |
| 2019/0001187 A1 * | 1/2019 | Costella | A61M 16/0006 |
| 2019/0247610 A1 * | 8/2019 | Costella | A61M 16/201 |

* cited by examiner

ID OF THE INVENTION

The present invention relates generally to a device and corresponding method of use in at least the sleep, fitness, medical, and physical therapy industries. More particularly, but not exclusively, the present invention relates to a breathing device with an exhale and inhale valve to create resistance which allows a user to strengthen his or her respiratory system over a period of time as a result of repeated use of the breathing device.

BACKGROUND OF THE INVENTION

The background description provided herein is for the purpose of generally presenting the context of the present disclosure. Work of the presently named inventors, to the extent the work is described in the present disclosure, as well as aspects of the description that may not otherwise qualify as prior art at the time of filing, are neither expressly nor impliedly admitted as prior art.

Sleep apnea, also spelled sleep apnoea, is a sleep disorder characterized by pauses in breathing or periods of shallow breathing during sleep. Each pause can last for a few seconds to a few minutes and they happen many times a night. In the most common form, this follows loud snoring. There may be a choking or snorting sound as breathing resumes. As the disorder disrupts normal sleep, those affected may experience sleepiness or feel tired during the day. In children it may cause problems in school, or hyperactivity.

There are three forms of sleep apnea: obstructive (OSA), central (CSA), and a combination of the two called mixed. OSA is the most common form. Risk factors for OSA include being overweight, a family history of the condition, allergies, a small airway, and enlarged tonsils. In OSA, breathing is interrupted by a blockage of airflow, while in CSA breathing stops due to a lack of effort to breathe. People with sleep apnea may not be aware they have it. In many cases, it is first observed by a family member. Sleep apnea is often diagnosed with an overnight sleep study and is typically diagnosed when more than five episodes per hour occur.

OSA affects 1 to 6% of adults and 2% of children. It affects males about twice as often as females. While people at any age can be affected, it occurs most commonly among those 55 to 60 years old. Central sleep apnea affects less than 1% of people.

Treatment may include lifestyle changes, mouthpieces, breathing devices, and surgery. Lifestyle changes may include avoiding alcohol, losing weight, stopping smoking, and sleeping on one's side. Breathing devices include the use of a CPAP machine. Without treatment, sleep apnea may increase the risk of heart attack, stroke, diabetes, heart failure, irregular heartbeat, obesity, and motor vehicle collisions.

Asthma is a common long-term inflammatory disease of the airways of the lungs. It is characterized by variable and recurring symptoms, reversible airflow obstruction, and bronchospasm. Symptoms include episodes of wheezing, coughing, chest tightness, and shortness of breath. These episodes may occur a few times a day or a few times per week. Depending on the person, they may become worse at night or with exercise.

Asthma is thought to be caused by a combination of genetic and environmental factors. Environmental factors include exposure to air pollution and allergens. Other potential triggers include medications such as aspirin and beta blockers. Diagnosis is usually based on the pattern of symptoms, response to therapy over time, and spirometry. Asthma is classified according to the frequency of symptoms, forced expiratory volume in one second (FEV1), and peak expiratory flow rate. It may also be classified as atopic or non-atopic, where atopy refers to a predisposition toward developing a type 1 hypersensitivity reaction.

In 2015, 358 million people globally had asthma, up from 183 million in 1990. It caused about 397,100 deaths in 2015, most of which occurred in the developing world. It often begins in childhood. The rates of asthma have increased significantly since the 1960s.

There is no cure for asthma. Symptoms can be prevented by avoiding triggers, such as allergens and irritants, and by the use of inhaled corticosteroids. Long-acting beta agonists (LABA) or antileukotriene agents may be used in addition to inhaled corticosteroids if asthma symptoms remain uncontrolled. Treatment of rapidly worsening symptoms is usually with an inhaled short-acting beta-2 agonist such as salbutamol and corticosteroids taken by mouth. In very severe cases, intravenous corticosteroids, magnesium sulfate, and hospitalization may be required. Those suffering from asthma sometimes seek alternative ways to manage their symptoms and thus turn to breathing devices to strengthen their respiratory system.

Conventional breathing devices used to address sleep apnea, asthma, or other debilitating diseases are typically, bulky, complex, and expensive to manufacture. Some of these conventional breathing devices cannot be taken apart or are extremely difficult to take apart. This can complicate the user's ability to replace broken or damaged parts, troubleshoot issues with the device, or even to simply clean the device. At the other end of the spectrum, some other conventional breathing devices require complete self-assembly and are not intuitively designed to facilitate quick assembly and disassembly. For example, some of the parts of these conventional devices can be assembled in a manner not originally intended by their manufacturers due to the overuse of similarly shaped components. This can cause the device to function at less than an optimal capacity or may cause the device to fall apart easily.

Other issues with conventional breathing devices include a limited ability to set an appropriate resistance level for best improving a user's respiratory system. For example, conventional breathing devices typically (a) do not provide enough resistance to meaningfully improve a user's respiratory system, (b) provide too much resistance and make it impossible for the user to breathe, which likely results in the user no longer using the device, (c) obfuscate what level of resistance the device is set at, and/or (d) make it too difficult to adjust the level of resistance to an appropriate level.

Thus, there exists a need in the art for a breathing device which simplifies the use and assembly of the device but does not allow the user the complete freedom to use or assemble the device in a manner not originally intended by the manufacturer.

SUMMARY OF THE INVENTION

Therefore, it is a primary object, feature, or advantage of the present invention to improve on or overcome the deficiencies in the art.

It is still yet a further object, feature, or advantage of the present invention to provide a breathing device that may be used in a wide variety of applications.

It is still yet a further object, feature, or advantage of the present invention to provide a breathing device that improves safety.

It is still yet a further object, feature, or advantage of the present invention to provide a breathing device that is cost effective.

It is still yet a further object, feature, or advantage of the present invention to provide a breathing device that is reliable and durable and has a long usable life.

It is still yet a further object, feature, or advantage of the present invention to provide a breathing device which is easily used and reused.

It is still yet a further object, feature, or advantage of the present invention to provide a breathing device that is easily manufactured, assembled, disassembled, repaired, replaced, stored, transported, and cleaned.

It is still yet a further object, feature, or advantage of the present invention to provide a breathing device that is aesthetically pleasing.

It is still yet a further object, feature, or advantage of the present invention to incorporate the breathing device into a system accomplishing some or all of the previously stated objectives.

It is still yet a further object, feature, or advantage of the present invention to provide methods of using, manufacturing, installing, repairing a breathing device accomplishing some or all of the previously stated objectives.

These or other objects, features, and advantages of the present invention will be apparent to those skilled in the art after reviewing the following detailed description of the illustrated embodiments, accompanied by the attached drawings.

Figure 1:
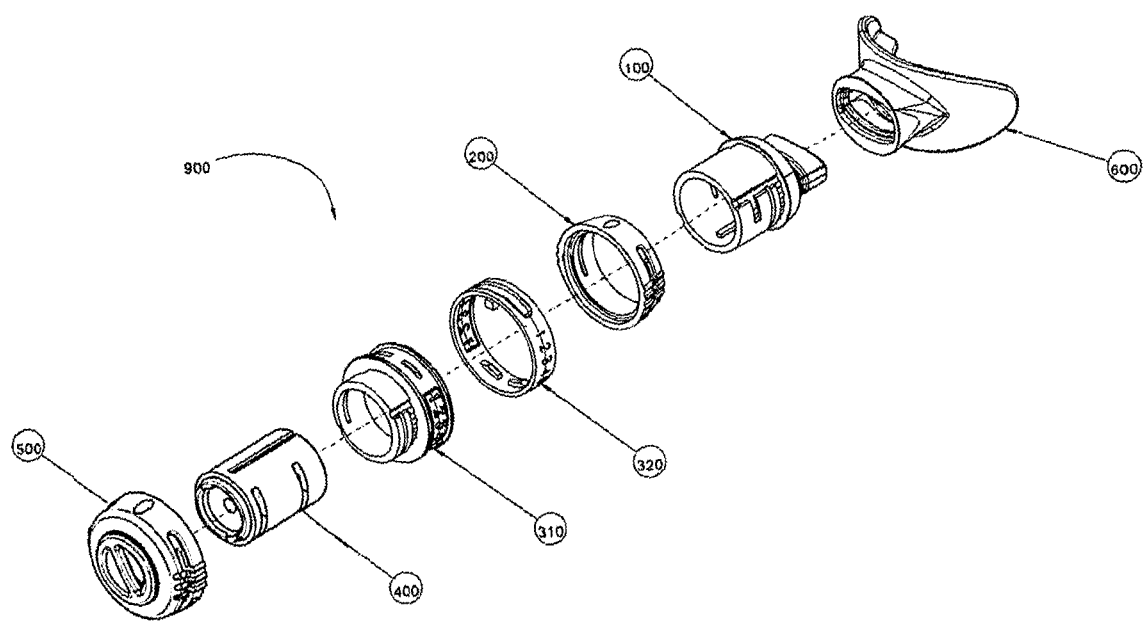
FIG. 1 shows an exploded view of a breathing device with an exhale and an inhale valve to create resistance, according to some aspects of the present disclosure.

Various embodiments of the present disclosure illustrate several ways in which the present invention may be practiced. These embodiments will be described in detail with reference to the drawings, wherein like reference numerals represent like parts throughout the several views. Reference to specific embodiments does not limit the scope of the present disclosure and the drawings represented herein are presented for exemplary purposes.

DETAILED DESCRIPTION OF THE INVENTION

The following definitions and introductory matters are provided to facilitate an understanding of the present invention. Unless defined otherwise, all technical and scientific terms used herein have the same meaning as commonly understood by one of ordinary skill in the art to which embodiments of the present invention pertain.

The terms "a," "an," and "the" include plural referents unless context clearly indicates otherwise. Similarly, the word "or" is intended to include "and" unless context clearly indicate otherwise. The word "or" means any one member of a particular list and also includes any combination of members of that list.

The terms "invention" or "present invention" as used herein are not intended to refer to any single embodiment of the particular invention but encompass all possible embodiments as described in the specification and the claims.

The term "about" as used herein refers to variation in the numerical quantities that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The claims include equivalents to the quantities whether or not modified by the term "about."

The term "configured" describes a device, system, or other structure that is constructed to perform or capable of performing a particular task or to adopt a particular configuration. The term "configured" can be used interchangeably with other similar phrases such as constructed, arranged, adapted, manufactured, and the like.

Terms such as first, second, vertical, horizontal, top, bottom, upper, lower, front, rear, end, sides, concave, convex, and the like, are referenced according to the views presented. These terms are used only for purposes of description and are not limiting unless these terms are expressly included in the claims. Orientation of an object or a combination of objects may change without departing from the scope of the invention.

The devices, systems, and methods of the present invention may comprise, consist essentially of, or consist of the components of the present invention described herein. The term "consisting essentially of" means that the devices, systems, and methods may include additional components or steps, but only if the additional components or steps do not materially alter the basic and novel characteristics of the claimed devices, systems, and methods.

The following embodiments are described in sufficient detail to enable those skilled in the art to practice the invention however other embodiments may be utilized. Mechanical, procedural, and other changes may be made without departing from the spirit and scope of the invention. Accordingly, the scope of the invention is defined only by the appended claims, along with the full scope of equivalents to which such claims are entitled.

FIG. 1 shows in an exploded view of each of the component subsystems which comprise a first embodiment of an improved breathing device 900. The component subsystems include a front piece 100, a mouth piece 600, an inhale ring 200 (also referred to as an inhale piece), a middle piece 310, an over-mold 320, an insert slider 400, and an exhale ring 500 (also referred to as an exhale piece).

The mouth piece 600 acts as an object which comes near or in contact with the user's mouth or nose during use. It may comprise rigid material, a flexible material, or some combination of both and include ridges such that the mouth piece 600 comfortably fit into the user's mouth. The material which makes up the mouth-piece should be non-toxic, and should not degrade after repeated use by the user (e.g. deform easily from biting, or wear easily due to a user's saliva). The mouthpiece 600 is preferably shaped such that there is almost no or an extremely minimal risk of causing the user to choke or gag. The mouthpiece 600 is designed in this manner so that the user does not dread using the device, so that there is an increased chance the user will use the device over long periods of time which is helpful in improving the user's respiratory system in order to improve the user's sleep.

Figure 2A:
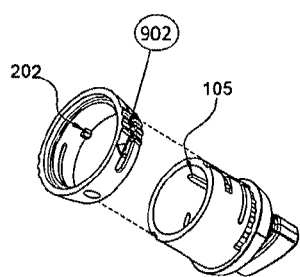
FIG. 2A shows a detailed perspective view of the front piece of the breathing device of FIG. 1, according to some aspects of the present disclosure.
Figure 2B:
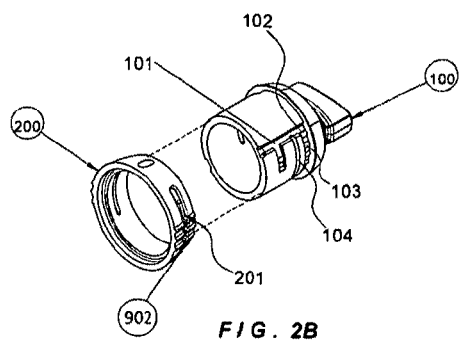
FIG. 2B shows an alternative detailed perspective view of the front piece of FIG. 2A, according to some aspects of the present disclosure.

FIGS. 2A-2B illustrate insertion of the inhale ring 200 into the front piece 100. The front piece 100 is typically a cylindrical body and comprises a non-toxic rigid material, such as plastic or a metallic alloy. As shown, the front piece 100 includes a front piece first groove 101 positioned on a lower circumferential edge of the cylindrical body, a first locking bump or protrusion 102, front piece incremental bumps or protrusions 103, a front piece channel or slot 104, and a front piece rib 105. The inhale ring 200 is typically an annular body and comprises a non-toxic rigid material, such as plastic or a metallic alloy. As shown, the inhale ring 200 includes an inhale ring channel or slot 201 and an inhale ring bump or protrusion 202 located on an internal surface of the annular body.

Figure 11A:
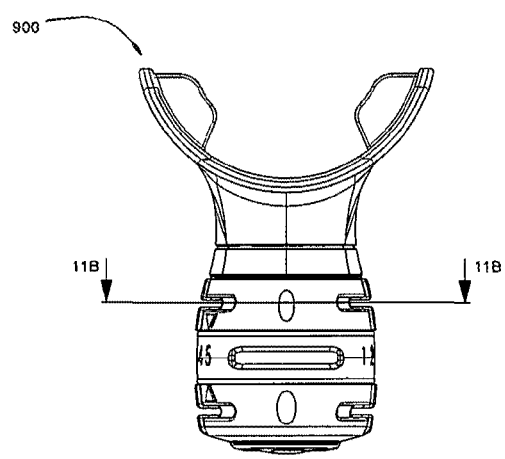
FIG. 11A shows a perspective view of some of components that facilitate opening and closing the breathing devices of FIGS. 1 and 8, according to some aspects of the present disclosure.
Figure 11B:
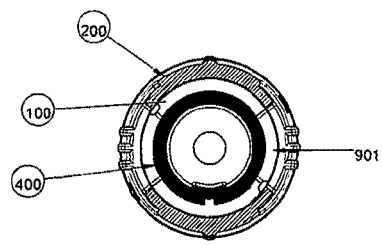
FIG. 11B shows a bottom plan view of some of components that facilitate opening and closing the breathing device of FIG. 11A, according to some aspects of the present disclosure.

In use, the inhale ring bump or protrusion 202 is inserted in the front piece first groove 101. Once fully inserted in the front piece first groove 101, the inhale ring 200 is rotated. The first locking bump or protrusion 102 is for locking the inhale ring 200 into place. In a preferred embodiment, the inhale ring must be locked into place before rotation of the inhale ring 200. There are typically four front piece incremental bumps or protrusions 103 which allow for rotating the inhale ring 200 in different five increments. The front piece incremental bumps or protrusions 103 may be uniformly spaced apart from one another, or they may have a more asymmetrical configuration. Once the inhale ring 200 is locked over the first locking bump or protrusion 102 and the inhale ring 200 is fully inserted over the front piece 100, the front piece channel or slot 104 is in the same plane as the inhale ring channel or slot 201. In the locked position, the front piece channel or slot 104 and the inhale ring channel or slot 201 are in completely different angular positions. As the inhale ring 200 is rotated over the front piece incremental bumps or protrusions 103, the front piece channel or slot 104 and the inhale ring channel or slot 201 start aligning until, at the end of rotating over all bump or protrusions, the front piece channel or slot 104 and the inhale ring channel or slot 201 are completely aligned. So, as the inhale ring 200 rotates, the opening created by the angular position of the slots (of the front piece 100 and the insert slider 400) gets widened, thus increasing the amount of air that flows through an air passage 901 of the overall improved breathing device 900 (see FIGS. 11A-11B). This increase or decrease of the width of the air passage 901 correlates to the resistance level for inhalation. During inhalation, if the width of the air passage 901 is smaller, the device provides more resistance to the lungs; if the width of the air passage 901 is larger, the device provides less resistance to the lungs.

Figure 3A:
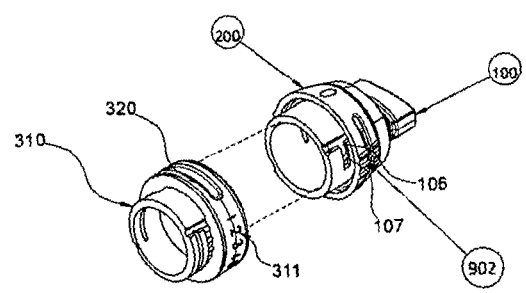
FIG. 3A shows a detailed perspective view of the middle piece of the breathing device of FIG. 1, according to some aspects of the present disclosure.
Figure 3B:
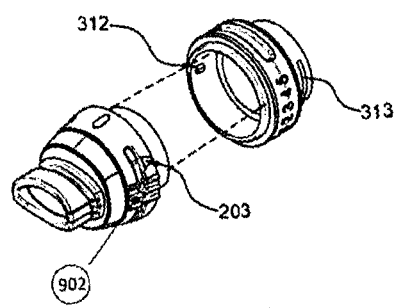
FIG. 3B shows an alternative detailed perspective view of the middle piece of FIG. 3A, according to some aspects of the present disclosure.

After the inhale ring 200 is inserted on the front piece 100 and locked, the middle piece 310 is slid over the front piece 100, as illustrated in FIGS. 3A-3B. The middle piece 310 is molded over by an over-mold 320 and includes numbers 311 (e.g., 1 to 5), a middle piece first locking bump or protrusion 312, a middle piece channel or slot 313, a middle piece groove 315, a middle piece second locking bump or protrusion 316, and middle piece incremental bumps or protrusions 317.

A middle piece first locking bump or protrusion 312 slides in the front piece first groove 101 and then rotated into the front piece second groove 106 and over the front piece second locking bump or protrusion 107 to lock. Once locked, the middle piece 310 remains stationary relative to the front piece 100. Thus, when the inhale ring is rotated, the inhale ring arrow 203 will point to the numbers on the middle piece 310, thereby indicating the resistance level to the user. The middle piece 310 utilizes the middle piece channel or slot 313 during exhaling to increase or decrease the resistance level in exhale blow, as will become apparent from a review of FIGS. 4 and 5A-5B.

Figure 4:
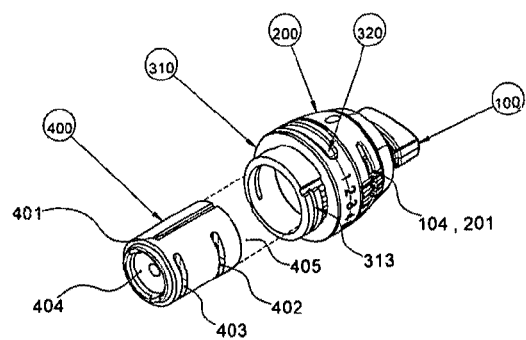
FIG. 4 shows a detailed perspective view of an insert slider of the breathing device of FIG. 1, according to some aspects of the present disclosure.
Figure 5A:
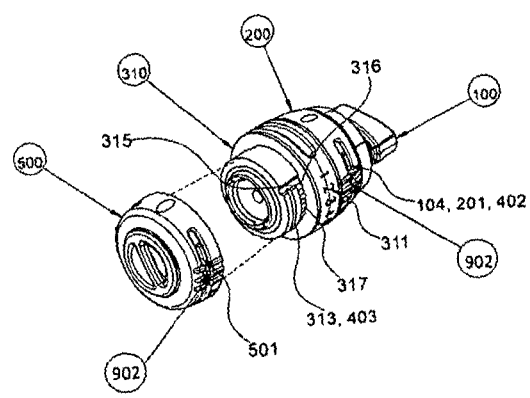
FIG. 5A shows a detailed perspective view of the exhale ring of the breathing device of FIG. 1, according to some aspects of the present disclosure.
Figure 5B:
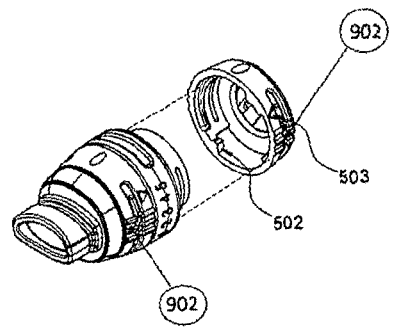
FIG. 5B shows an alternative detailed perspective view of the exhale ring of FIG. 5A, according to some aspects of the present disclosure.

FIGS. 4 and 5A-5B show a first embodiment of an insert slider 400 which is insertable into the front piece 100. The insert slider 400 has an insert slider groove 401, an insert slider first channel or slot 402, an insert slider second channel or slot 403, an insert slider closed end 404, and an insert slider open end 405. The insert slider groove 401 includes a groove closed end. The insert slider first channel or slot 402 matches with the front piece channel or slot 104. The insert slider groove 401 matches with the front piece rib 105 (as shown in FIGS. 2A-2B). Thus, there is no angular movement of the slider due to this groove and ring engagement. The insert slider 400 can slide inside the front piece 100. The insert slider first channel or slot 402 matches with the middle piece channel or slot 313. As the user inhales, the insert slider 400 moves inside, forward, and towards the user's mouth. In this position, the insert slider first channel or slot 402 matches with the front piece channel or slot 104.

Figure 7:
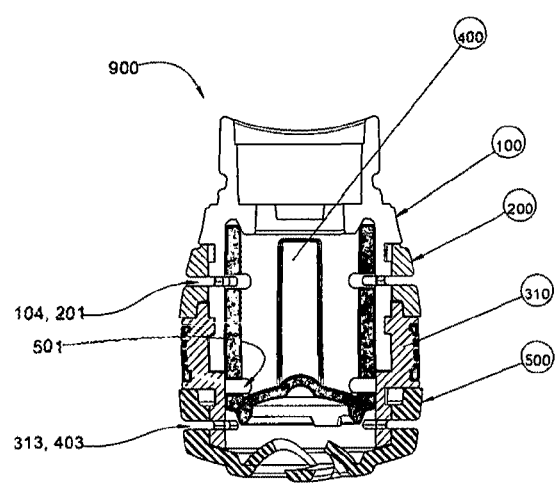
FIG. 7 shows a front plan view of the breathing device of FIG. 1 in an inhale position, according to some aspects of the present disclosure.

The various channels or slots 104, 201, and 402 align during the inhale movement, as shown in FIGS. 5A-5B and 7.

The exhale ring 500 is typically an annular body closed at one end like a cap and comprises a non-toxic rigid material, such as plastic or a metallic alloy. The exhale ring 500 includes an exhale ring channel or slot 501, an exhale ring bump or protrusion 502, and an exhale ring arrow 503. The exhale ring 500 is mountable on the middle piece. Similar to the inhale ring, the exhale ring in the improved breathing device 900 is shown with ridges which form grips 902. Ridges exemplify only one way to form the grips 902. More particularly, the grips 902 may comprise any material which assists the user in gripping the tool. Thus, in some alternative embodiments, the grips 902 may be formed of knurling, specially shaped grooves, partially adhesive substances, other materials or objects which provide a tactile effect, strap(s), other known gripping mechanisms, or any combination thereof, as shown in FIGS. 2A-2B, 3A-3B, and 5A-5B.

Figure 6:
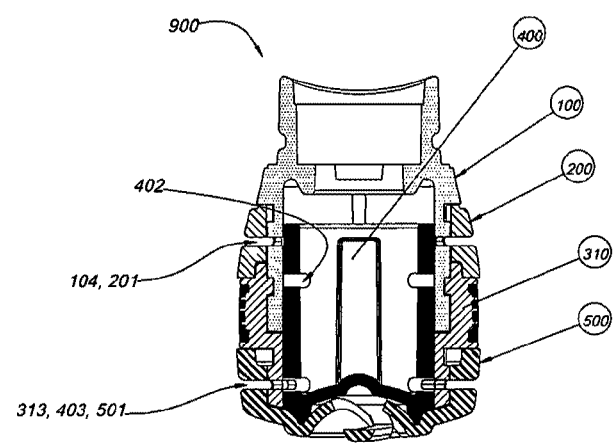
FIG. 6 shows a front plan view of the breathing device of FIG. 1 in an exhale position, according to some aspects of the present disclosure.

When the exhale ring 500 is mounted on the middle piece 310, the exhale ring slot 501 aligns with the middle piece channel or slot 313. The exhale ring bump or protrusion 502 engages with the middle piece groove 315. The exhale ring 500 can then be rotated over a middle piece second locking bump or protrusion 316 to lock. The exhale ring can then rotate to adjust to five different increments as the exhale ring 500 rotates over four middle piece incremental bumps or protrusions 317. As the rings rotate, the exhale ring arrow 503 points to the numbers 311, thus indicating different resistance levels to the user. As the exhale ring 500 rotates, the exhale ring channel or slot 501 starts aligning with the middle piece channel or slot 313, thus increasing the width of the air passage. When the user exhales, the slider moves outside, backward, and away from the user's mouth, thereby aligning the various channels or slots 313, 403, and 501 in one plane, as shown in FIG. 6.

Figure 8:
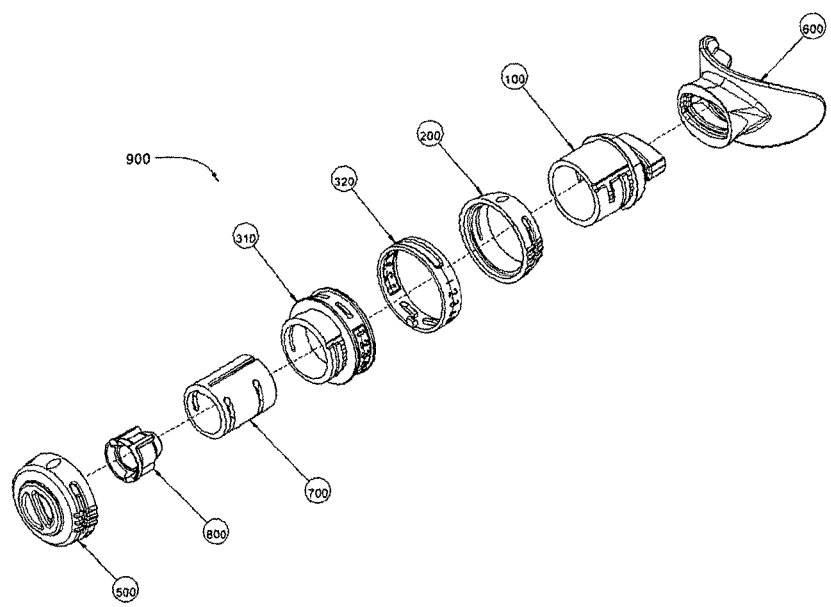
FIG. 8 shows an exploded view of an alternative breathing device with an exhale and an inhale valve to create resistance, according to some aspects of the present disclosure.

FIG. 8 shows in an exploded view each of the component subsystems which comprise a second embodiment of an improved breathing device 900. The component subsystems include a front piece or insertable mouth piece 100, an inhale ring 200, a middle piece 310, an over-mold 320, an alternative insert slider main piece 700, a slider add-on 800, and an exhale ring 500.

Figure 9:
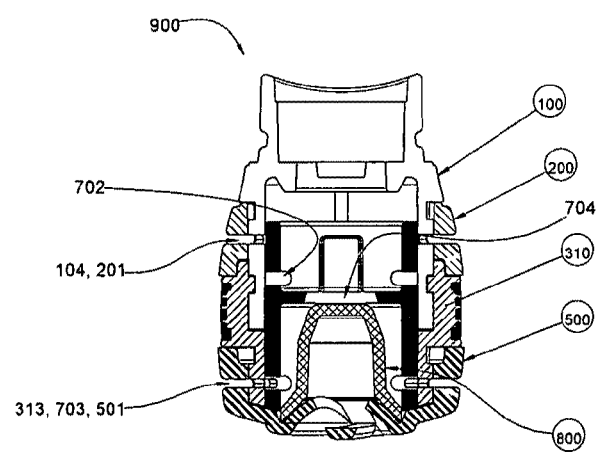
FIG. 9 shows a front plan view of the alternative breathing device of FIG. 8 in an exhale position, according to some aspects of the present disclosure.

In the second embodiment, two slider components are utilized instead of one. The alternative insert slider main piece 700 functions similarly to the insert slider 400 of the first embodiment. As the user exhales, the alternative slider main piece 700 moves away from the user's mouth, thereby blocking the front piece channel or slot 104 and the inhale ring channel or slot 201. In the exhale position, the alternative insert slider first channel or slot 702 does not align with the front piece channel or slot 104 or the inhale ring channel or slot 201. Instead, the opening 704 remains open, and the various channels or slots 313, 501, and 703 align. Thus, the air blown by the user passes through the opening 704 and then through the various channels or slots 313, 501, and 703, as is shown in FIG. 9.

Figure 10:
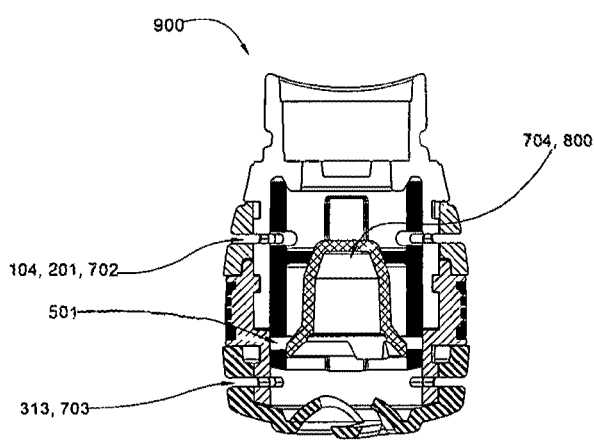
FIG. 10 shows a front plan view of the alternative breathing device of FIG. 8 in an inhale position, according to some aspects of the present disclosure.

In the second embodiment, when the user inhales, the alternative insert slider main piece 700 moves towards the user's mouth and the slider add-on 800 blocks the opening 704. In this position, the exhale ring channel or slot 501 is completely blocked. Thus, only the combination of the three various channels or slots 104, 201, and 702 remain in play, as is shown in FIG. 10.

From the foregoing, it can be seen that the present invention accomplishes at least all of the stated objectives.

LIST OF REFERENCE NUMERALS

The following list of reference numerals is provided to facilitate an understanding and examination of the present disclosure and is not exhaustive. Provided it is possible to do so, elements identified by a numeral may be replaced or used in combination with any elements identified by a separate numeral. Additionally, numerals are not limited to the descriptors provided herein and include equivalent structures and other objects possessing the same function.

100 front piece
101 front piece first groove
102 front piece first locking bump or protrusion
103 front piece incremental bumps or protrusions
104 front piece channel or slot
105 front piece rib
106 front piece second groove
107 front piece second locking bump or protrusion
200 inhale ring/inhale piece
201 inhale ring channel or slot
202 inhale ring bump or protrusion
203 inhale ring arrow
310 middle piece
311 numbers
312 middle piece first locking bump or protrusion
313 middle piece channel or slot
315 middle piece groove
316 middle piece second locking bump or protrusion
317 middle piece incremental bumps or protrusions
320 over-mold
400 insert slider
401 insert slider groove
402 insert slider first channel or slot
403 insert slider second channel or slot
404 insert slider closed end
405 insert slider open end
500 exhale ring/exhale piece
501 exhale ring channel or slot
502 exhale ring bump or protrusion
503 exhale ring arrow
600 mouth piece
700 alternative insert slider main piece
702 alternative insert slider first channel or slot
703 alternative insert slider second channel or slot
704 opening
800 slider add-on
900 an improved breathing device
901 air passage
902 Ridges on the inhale and exhale pieces which form the grips The present disclosure is not to be limited to the particular embodiments described herein. The following claims set forth a number of the embodiments of the present disclosure with greater particularity.

What is claimed is:
1. A breathing device comprising:
   a mouthpiece;
   a front piece coupled to the mouthpiece, the front piece comprising:
      a front piece first groove on an outer surface of the front piece;
      a front piece first locking bump;
      front piece incremental bumps,
      a front piece channel;

a front piece rib on an inner surface of the front piece;
a front piece second groove on the outer surface of the front piece; and
a front piece second locking bump;
an inhale ring comprising:
an inhale ring channel rotatable with respect to the front piece channel; and
an inhale ring bump insertable into the front piece first groove;
a middle piece comprising:
a middle piece first locking bump insertable into the front piece second groove;
a middle piece channel;
a middle piece rib on an inner surface of the middle piece;
a middle piece groove on an outer surface of the middle piece;
a middle piece second locking bump; and
middle piece incremental bumps;
an insert slider being slidable between an inhale position and an exhale position, the insert slider comprising:
an insert slider groove on an outer surface of the insert slider capable of mating with the front piece rib and the middle piece rib;
an insert slider first channel rotatable with respect to the front piece channel and the inhale ring channel; and
an insert slider second channel rotatable with respect to the middle piece channel; and
an exhale ring comprising:
an exhale ring channel rotatable with respect to the middle piece channel and the insert slider second channel; and
an exhale ring bump insertable into the middle piece groove.

2. The breathing device of claim 1 further comprising an over-mold covering the middle piece.

3. The breathing device of claim 1 further comprising numbers on the middle piece to identify an overall level of resistance of the breathing device.

4. The breathing device of claim 1 further comprising arrows on the inhale ring and the exhale ring that point towards the numbers.

5. The breathing device of claim 1 wherein the breathing device is settable to several different levels of resistance as the inhale ring bump rotates over the front piece incremental bumps.

6. The breathing device of claim 1 wherein the breathing device is settable to several different levels of resistance as the exhale ring bump rotates over the middle piece incremental bumps.

7. The breathing device of claim 1 wherein the insert slider further comprises a main piece and an add-on.

8. The breathing device of claim 1 wherein the inhale ring channel is only rotatable with respect to the front piece channel once the inhale ring bump is inserted into front piece first groove.

9. The breathing device of claim 1 wherein the exhale ring channel is only rotatable with respect to the middle piece channel once the exhale ring bump is inserted into middle piece groove.

10. The breathing device of claim 1 wherein the inhale ring is locked to the front piece when the inhale ring bump is rotated over the front piece first locking bump.

11. The breathing device of claim 1 wherein the middle piece is locked to the front piece when the middle piece first locking bump is rotated over the front piece second locking bump.

12. The breathing device of claim 1 wherein the exhale ring is locked to the middle piece when the exhale ring bump is rotated over the middle piece second locking bump.

13. The breathing device of claim 1 wherein a first opening created by a first angular position between the front piece channel, the inhale ring channel, and the insert slider first channel partially determines a first amount of air that flows through an air passage of the breathing device.

14. The breathing device of claim 13 wherein a second opening created by a second angular position between the middle piece channel, the insert slider second channel, and the exhale ring channel partially determines a second amount of air that flows through the air passage of the breathing device.

15. A method of adjusting the resistance of the breathing device of claim 14, comprising:
changing the first angular position between the front piece channel, the inhale ring channel, and the insert slider first channel; or
changing the second angular position between the middle piece channel, the insert slider second channel, and the exhale ring channel.

16. The method of claim 15 further comprising assembling the breathing device.

17. The method of claim 16 wherein the middle piece is insertable into the breathing device in only a single configuration.

18. A method of using the breathing device of claim 1 comprising:
inhaling through the breathing device; and
exhaling through the breathing device.

19. The method of claim 18 wherein inhaling causes the insert slider to move into the inhale position and exhaling causes the insert slider to move into the exhale position.

* * * * *